United States Patent
Schuck (10) Patent No.: US 8,474,691 B2
(45) Date of Patent: Jul. 2, 2013

(54) SYSTEM, APPARATUS, METHOD AND COMPUTER-READABLE STORAGE MEDIUM FOR GENERATING MEDICATION LABELS

(75) Inventor: Joseph C. Schuck, McMurray, PA (US)

(73) Assignee: McKesson Automation Inc., Cranberry, PA (US)

( * ) Notice: Subject to any disclaimer, the term of this patent is extended or adjusted under 35 U.S.C. 154(b) by 509 days.

(21) Appl. No.: 12/751,556

(22) Filed: Mar. 31, 2010

(65) Prior Publication Data

US 2011/0240729 A1    Oct. 6, 2011

(51) Int. Cl.
*G06F 17/00* (2006.01)

(52) U.S. Cl.
USPC ............................................ 235/375

(58) Field of Classification Search
USPC ............................................ 235/375
See application file for complete search history.

(56) References Cited

U.S. PATENT DOCUMENTS

| | | |
|---|---|---|
| 4,717,042 A | 1/1988 | McLaughlin |
| 4,785,969 A | 11/1988 | McLaughlin |
| 4,847,764 A | 7/1989 | Halvorson |
| 5,014,875 A | 5/1991 | McLaughlin et al. |
| 5,190,185 A | 3/1993 | Blechl |
| 5,314,243 A | 5/1994 | McDonald et al. |
| 5,346,297 A | 9/1994 | Colson, Jr. et al. |
| 5,377,864 A | 1/1995 | Blechl et al. |
| 5,405,048 A | 4/1995 | Rogers et al. |
| 5,431,299 A | 7/1995 | Brewer et al. |
| 5,460,294 A | 10/1995 | Williams |
| 5,468,110 A | 11/1995 | McDonald et al. |
| 5,480,062 A | 1/1996 | Rogers et al. |
| 5,520,450 A | 5/1996 | Colson, Jr. et al. |
| 5,564,803 A | 10/1996 | McDonald et al. |
| 5,593,267 A | 1/1997 | McDonald et al. |
| 5,661,978 A | 9/1997 | Holmes et al. |
| D384,578 S | 10/1997 | Wangu et al. |
| 5,713,485 A | 2/1998 | Liff et al. |
| 5,716,114 A | 2/1998 | Holmes et al. |
| 5,745,366 A | 4/1998 | Higham et al. |
| 5,761,877 A | 6/1998 | Quandt |
| 5,797,515 A | 8/1998 | Liff et al. |
| 5,805,456 A | 9/1998 | Higham et al. |
| 5,842,976 A | 12/1998 | Williamson |
| 5,878,885 A | 3/1999 | Wangu et al. |
| 5,880,443 A | 3/1999 | McDonald et al. |
| 5,883,806 A | 3/1999 | Meador et al. |
| 5,893,697 A | 4/1999 | Zini et al. |
| 5,905,653 A | 5/1999 | Higham et al. |
| 5,912,818 A | 6/1999 | McGrady et al. |

(Continued)

*Primary Examiner* — Thien M Le
*Assistant Examiner* — April Taylor
(74) *Attorney, Agent, or Firm* — Alston & Bird LLP (57) ABSTRACT

An apparatus is provided that includes a processor configured to at least perform or cause the apparatus to at least perform a number of functions. The functions include storing an order log for a fill order specifying a medication in a receptacle including an affixed label having a printed pattern of machine-readable dots or markings. The functions also include receiving a digitized signature, initials or marking handwritten on the label and captured by a digital pen based on the pattern printed on the label. The digital pen is registered to a user, and the signature/initials/marking reflects verification by the user that the medication in the receptacle is correct. Recording the events or activities also includes authenticating the user as having authority to verify the fill order based on the registration of the digital pen to the user, and when authenticated, recording the digitized signature/initials/marking in the order log.

19 Claims, 5 Drawing Sheets

U.S. PATENT DOCUMENTS

| | | | |
|---|---|---|---|
| 5,927,540 | A | 7/1999 | Godlewski |
| 5,940,306 | A | 8/1999 | Gardner et al. |
| 5,971,593 | A | 10/1999 | McGrady |
| 6,003,006 | A | 12/1999 | Colella et al. |
| 6,011,999 | A | 1/2000 | Holmes |
| 6,021,392 | A | 2/2000 | Lester et al. |
| 6,039,467 | A | 3/2000 | Holmes |
| 6,065,819 | A | 5/2000 | Holmes et al. |
| 6,068,156 | A | 5/2000 | Liff et al. |
| 6,109,774 | A | 8/2000 | Holmes et al. |
| 6,112,502 | A | 9/2000 | Frederick et al. |
| 6,116,461 | A | 9/2000 | Broadfield et al. |
| 6,151,536 | A | 11/2000 | Arnold et al. |
| 6,170,230 | B1 | 1/2001 | Chudy et al. |
| 6,176,392 | B1 | 1/2001 | William et al. |
| 6,189,727 | B1 | 2/2001 | Shoenfeld |
| 6,223,934 | B1 | 5/2001 | Shoenfeld |
| 6,256,967 | B1 | 7/2001 | Hebron et al. |
| 6,283,322 | B1 | 9/2001 | Liff et al. |
| 6,289,656 | B1 | 9/2001 | Wangu et al. |
| 6,338,007 | B1 | 1/2002 | Broadfield et al. |
| 6,339,732 | B1 | 1/2002 | Phoon et al. |
| 6,361,263 | B1 | 3/2002 | Dewey et al. |
| 6,370,841 | B1 | 4/2002 | Chudy et al. |
| 6,449,927 | B2 | 9/2002 | Hebron et al. |
| 6,471,089 | B2 | 10/2002 | Liff et al. |
| 6,497,342 | B2 | 12/2002 | Zhang et al. |
| 6,499,270 | B2 | 12/2002 | Peroni et al. |
| 6,532,399 | B2 | 3/2003 | Mase |
| 6,564,121 | B1 | 5/2003 | Wallace et al. |
| 6,581,798 | B2 | 6/2003 | Liff et al. |
| 6,609,047 | B1 | 8/2003 | Lipps |
| 6,611,733 | B1 | 8/2003 | De La Huerga |
| 6,625,952 | B1 | 9/2003 | Chudy et al. |
| 6,640,159 | B2 | 10/2003 | Holmes et al. |
| 6,650,964 | B2 | 11/2003 | Spano, Jr. et al. |
| 6,671,579 | B2 | 12/2003 | Spano, Jr. et al. |
| 6,681,149 | B2 | 1/2004 | William et al. |
| 6,742,671 | B2 | 6/2004 | Hebron et al. |
| 6,755,931 | B2 | 6/2004 | Vollm et al. |
| 6,760,643 | B2 | 7/2004 | Lipps |
| 6,776,304 | B2 | 8/2004 | Bossi et al. |
| 6,785,589 | B2 | 8/2004 | Eggenberger et al. |
| 6,790,198 | B1 | 9/2004 | White et al. |
| 6,814,254 | B2 | 11/2004 | Liff et al. |
| 6,814,255 | B2 | 11/2004 | Liff et al. |
| 6,847,861 | B2 | 1/2005 | Lunak et al. |
| 6,874,684 | B1 | 4/2005 | Denenberg et al. |
| 6,892,780 | B2 | 5/2005 | Vollm et al. |
| 6,895,304 | B2 | 5/2005 | Spano, Jr. et al. |
| 6,975,922 | B2 | 12/2005 | Duncan et al. |
| 6,985,797 | B2 | 1/2006 | Spano, Jr. et al. |
| 6,996,455 | B2 | 2/2006 | Eggenberger et al. |
| 7,010,389 | B2 | 3/2006 | Lunak et al. |
| 7,014,063 | B2 | 3/2006 | Shows et al. |
| 7,016,766 | B2 | 3/2006 | William et al. |
| 7,040,504 | B2 | 5/2006 | Broadfield et al. |
| 7,052,097 | B2 | 5/2006 | Meek, Jr. et al. |
| 7,072,737 | B2 | 7/2006 | Lunak et al. |
| 7,072,855 | B1 | 7/2006 | Godlewski et al. |
| 7,077,286 | B2 | 7/2006 | Shows et al. |
| 7,085,621 | B2 | 8/2006 | Spano, Jr. et al. |
| 7,092,796 | B2 | 8/2006 | Vanderveen |
| 7,093,755 | B2 | 8/2006 | Jordan et al. |
| 7,100,792 | B2 | 9/2006 | Hunter et al. |
| 7,103,419 | B2 | 9/2006 | Engleson et al. |
| 7,111,780 | B2 * | 9/2006 | Broussard et al. ............ 235/381 |
| 7,139,639 | B2 | 11/2006 | Broussard et al. |
| 7,150,724 | B2 | 12/2006 | Morris et al. |
| 7,171,277 | B2 | 1/2007 | Engleson et al. |
| 7,218,231 | B2 | 5/2007 | Higham |
| 7,228,198 | B2 | 6/2007 | Vollm et al. |
| 7,249,688 | B2 | 7/2007 | Hunter et al. |
| 7,348,884 | B2 | 3/2008 | Higham |
| 7,417,729 | B2 | 8/2008 | Greenwald |
| 7,419,133 | B2 | 9/2008 | Clarke et al. |
| 7,426,425 | B2 | 9/2008 | Meek, Jr. et al. |
| 7,554,449 | B2 | 6/2009 | Higham |
| 7,571,024 | B2 | 8/2009 | Duncan et al. |
| 7,588,167 | B2 | 9/2009 | Hunter et al. |
| 2006/0267965 | A1 | 11/2006 | Clary |
| 2008/0255882 | A1 * | 10/2008 | Chin et al. ........................ 705/3 |
| 2008/0306740 | A1 | 12/2008 | Schuck et al. |
| 2009/0108072 | A1 * | 4/2009 | Wang ...................... 235/462.41 |
| 2009/0166415 | A1 | 7/2009 | Braun et al. |
| 2009/0194987 | A1 | 8/2009 | Christie et al. |

* cited by examiner

SYSTEM, APPARATUS, METHOD AND COMPUTER-READABLE STORAGE MEDIUM FOR GENERATING MEDICATION LABELS

FIELD

Exemplary embodiments of the present invention generally relate to generating medication labels and reports, and more particularly, to generating medication labels and reports in a manner enabling the capture, recordation and analysis of handwritten information from the respective labels and reports.

BACKGROUND

In a typical hospital, nursing home, or other similar institution, doctors visit their patients on a routine basis and prescribe various medications for each patient. In turn, patients may be placed on respective, patient-specific medication treatment plans that require that the patients take one or more doses of various medications daily. Some medications may require that they be administered only at certain times of the day (e.g., after meals) and/or at intervals of one or more hours each day. In addition, patients may request certain medications on an elective basis for complaints, such as head or body aches. These requests may be included with the doctor's medication request or prescription that the doctor sends to a pharmacy of the hospital for filling.

Medication requests or prescriptions received by the pharmacy are typically checked by a registered pharmacist and then entered into the pharmacy information system (PIS). These requests may reflect not only orders that are added to a particular patient's treatment plan, but also changes in a patient's existing treatment plan. The pharmacy information system combines this information with the patient's existing medication schedule and develops a patient medication profile. Using the patient medication profile, a fill list can be created that lists all medications that must be distributed to all patients for a given time period (e.g., a day).

In some instances, this list is printed and used by a pharmacist or pharmacy technician to hand pick each of the drugs needed for each patient (in the form of unit doses) and place those drugs in corresponding patient-specific medication receptacles (e.g., boxes, bins or bags), which may be labeled to identify the patient and drugs contained therein. A registered pharmacist then checks the accuracy of the patient order, and, assuming the order was accurate, the individual patient boxes are loaded into a large transport cart and delivered to a nursing unit.

As an alternative to the aforementioned manual pick process, a number of pharmacies utilize automated systems for dispensing and restocking inventory. However, not all pharmacies can afford or in some cases need such an automated system. These pharmacies instead rely on paper order forms and handwritten logs to order, deliver medications and keep inventory records. This is time consuming, inaccurate and lacks to the ability to electronically store, retrieve and analyze these activities. One operation that even automated pharmacies continue to compromise in this way is the aforementioned pharmacist checking process. Upon being checked by a pharmacist, reports and/or patient labels may be merely initialed by the pharmacist. Exceptions or other deviations from the reports and/or labels are seldom recorded, and reports and labels may be lost with time.

BRIEF SUMMARY

In light of the foregoing background, exemplary embodiments of the present invention provide an improve apparatus and method for generating medication labels and reports ("exemplary" as used herein referring to "serving as an example, instance or illustration"). According to one aspect of exemplary embodiments of the present invention, an apparatus is provided that includes a processor configured to at least perform or cause the apparatus to at least perform a number of functions. As recited, these functions include storing an order log for a fill order specifying a medication, where the fill order being completed includes producing a receptacle including the medication. The receptacle includes an affixed label having, printed thereon, (1) one or more pieces of information related to the fill order, and (2) a pattern of machine-readable dots or markings enabling capture and digitization of handwriting information input onto the label.

Also according to this aspect, the functions include recording, in the order log, one or more events or activities related to the fill order. Recording the events or activities includes receiving a digitized signature, initials or marking handwritten on the label and captured by a digital pen, such as a first digital pen, based on the pattern printed on the label. The digital pen is registered to a user, and the signature, initials or marking reflect verification by the user that the medication in the receptacle is correct relative to the fill order. In this regard, recording the events or activities also includes authenticating the user as having authority to verify the fill order based on the registration of the digital pen to the user, and recording the digitized signature, initials or marking in the order log when the user is authenticated.

The recording of events or activities may further include receiving a digitized correction or change to information on the label, which correction or change has been handwritten on the label and captured by a second digital pen based on the pattern printed on the label. The second digital pen may be registered to a second user, and the correction or change may reflect a correction or change to one or more of the pieces of information printed on the label. In such instances, then, the functions may also include authenticating the second user as having authority to correct or change the fill order based on the registration of the second digital pen to the second user, and recording the correction or change in the order log when the second user is authenticated.

The recording of events or activities may further include receiving a digitized first acknowledgement handwritten on the label and captured by a second digital pen based on the pattern printed on the label, and receiving a digitized second acknowledgement handwritten on the label and captured by a third digital pen based on the pattern printed on the label. The second digital pen may be registered to a second user, and the first acknowledgement may reflect receipt of the receptacle by the second user. Similarly, the third digital pen may be registered to a third user, and the second acknowledgement may reflect dispensing of the medication in the receptacle by the third user. In these instances, the functions may also include recording the first and second acknowledgements in the order log.

According to various exemplary embodiments, registering the digital pens to users may permit locating the receptacle within an institution such as a hospital. In this regard, the first, second and third users may associated with respective first, second and third areas of the institution. The processor, then, may be further configured to perform, cause the apparatus to perform or facilitate performance of locating the receptacle after recording one of the digitized signature, initials or marking, recording the first acknowledgement or recording the second acknowledgement. In these instances, the receptacle may be located relative to the first, second or third area based on the signature, initials or marking, first acknowledgment or second acknowledgement of the first, second or third user having been recorded before locating the receptacle.

In addition to or in lieu of utilizing the digital pen registration to locate the receptacle, the label may further include a radio frequency identification (RFID) tag configured to encode one or more of the pieces of information printed on the label. In these instances, recording one or more events or activities may further include locating the receptacle within an institution at one or more instances based on communication of the RFID tag with a radio frequency (RF) network operable within the institution; and may include recording the location of the receptacle at the one or more instances in the order log.

As indicated above and explained below, exemplary embodiments of the present invention may solve problems identified by prior techniques and provide additional advantages.

BRIEF DESCRIPTION OF THE DRAWINGS

Having thus described the invention in general terms, reference will now be made to the accompanying drawings, which are not necessarily drawn to scale, and wherein:

DETAILED DESCRIPTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
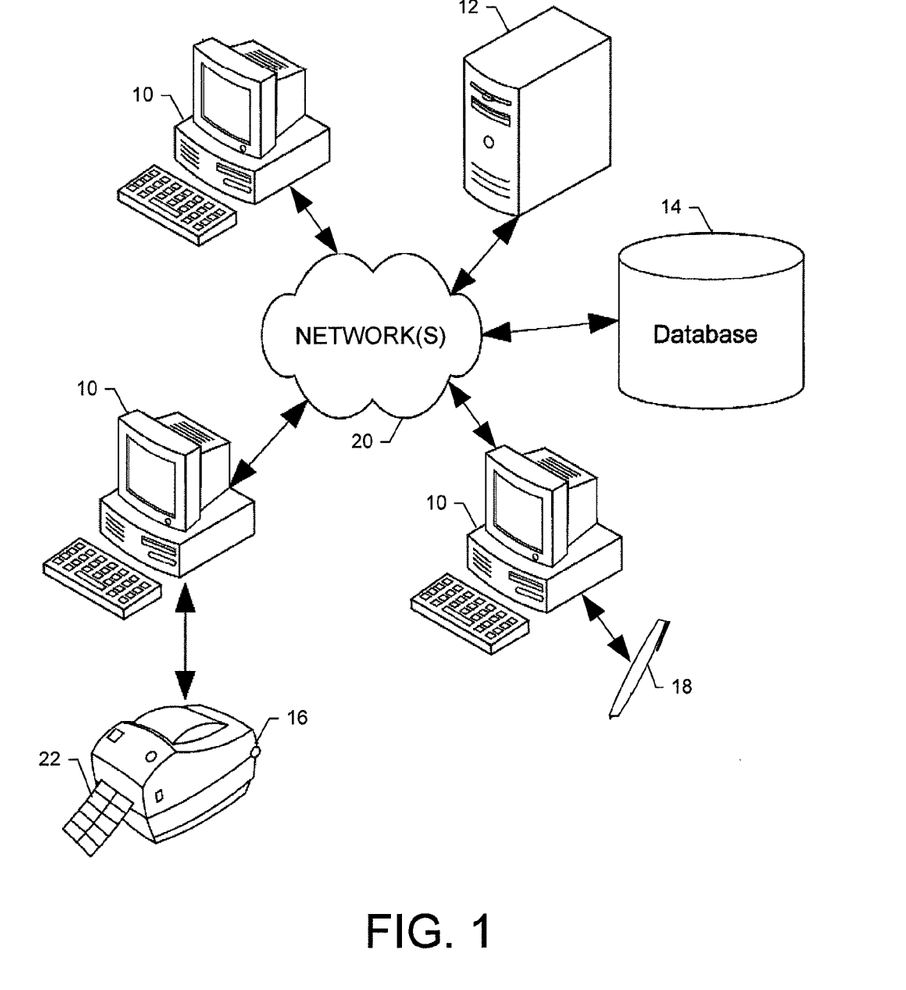
FIG. 1 is a schematic block diagram of a system configured to operate in accordance with exemplary embodiments of the present invention.

Referring to FIG. 1, an illustration of one type of system that may benefit from exemplary embodiments of the present invention is provided. As shown, the system may include at least one computing apparatus 10, which may be configured to operate in association with a medication storage device that may include one or more drawers, shelves, bins or the like for storing various medications. In this regard, the computing apparatus may be configured to generate labels for the medication storage device and/or medication receptacles within which medications from the medication storage device may be placed, in accordance with an embodiment of the present invention. Examples of suitable medication storage devices include medication carts or cabinets, nurse servers, various types of pharmacy medication storage equipment (e.g., a medication carousels, medication shelving, etc.) or the like; and examples of suitable medication receptacles include pill bottles, bins, boxes, bags, syringes, medicine cups, basins, vials, test tubes or the like.

The computing apparatus 10 is configured to directly and/or indirectly communicate with one or more other components of the system including, for example, one or more other computing apparatuses, server apparatuses 12, databases 14, printers 16 and/or digital pens 18 or the like. The components of the system, including the computing apparatus, server apparatus, database, printer and/or digital pen, may be configured to communicate with one another in accordance with any of a number of wireline or wireless communication or networking techniques. Examples of such techniques include, without limitation, Universal Serial Bus (USB), radio frequency (RF), Bluetooth (BT), infrared (IrDA), any of a number of different cellular (wireless) communication techniques such as any of a number of 2G, 2.5G or 3G communication techniques, local area network (LAN), wireless LAN (WLAN) techniques or the like. In accordance with various ones of these techniques, the components may be coupled to and configured to communicate across one or more networks 20. The network(s) can comprise any of a number of different combinations of one or more different types of networks, including data and/or voice networks. For example, the network(s) can include one or more data networks, such as a LAN, a metropolitan area network (MAN), and/or a wide area network (WAN) (e.g., Internet), and include one or more voice networks, such as a public-switched telephone network (PSTN). Although not shown, the network(s) may include one or more apparatuses such as one or more routers, switches or the like for relaying data, information or the like between the components of the system.

The computing apparatus 10, server apparatus 12, database 14, printer 16 and/or digital pen 18 may comprise any one or more of a number of different entities, devices or the like configured to operate in accordance with embodiments of the present invention. In this regard, one or more of the computing apparatus or server apparatus can comprise, include or be embodied in one or more processing elements, such as one or more of a laptop computer, desktop computer, server computer or the like. Additionally or alternatively, one or more of the computing apparatus or server apparatus can comprise, include or be embodied in one or more portable electronic devices, such as one or more of a portable music player, mobile telephone, portable digital assistant (PDA) or the like.

The printer 16 may comprise, include or be embodied in any of a number of different devices configured to print information generated by others of the components of the system. In one particular example described herein, the printer may be configured to the print the computing apparatus-generated labels 22 for the medication storage device and/or medication receptacles, and which may be affixed to or otherwise situated on or proximate the respective medication storage device and/or medication receptacles. Additionally or alternatively, the printer may be configured to print patient barcode labels, fill orders, various reports directed to the medication storage device, medications, patients or the like. The printer may be configured to communicate with the other components in any of the manners described above, and may further include a print server or the like for enabling communication across a network 20.

The digital pen 18 may comprise, include or be embodied in any of a number of different devices configured to capture and process and/or communicate handwritten information as described hereinbelow. The digital pen may be configured to communicate with others of the system components via a network 20 as described above. Additionally or alternatively, the digital pen may be configured to interface with a cradle which, in turn, may be configured to communicate with others of the system components, such as wirelessly via the network or more directly such as by means of a Universal Serial Bus (USB) or RS232 connection or the like. Examples of suitable digital pens include any of a number of digital pens implementing Anoto functionality such as, for example, digital pens offered by Anoto Group AB, Hewlett-Packard, Hitachi Maxell Ltd. Livescribe, Logitech Inc., Nokia Corporation and Sony Ericsson Mobile Communications AB.

Figure 2:
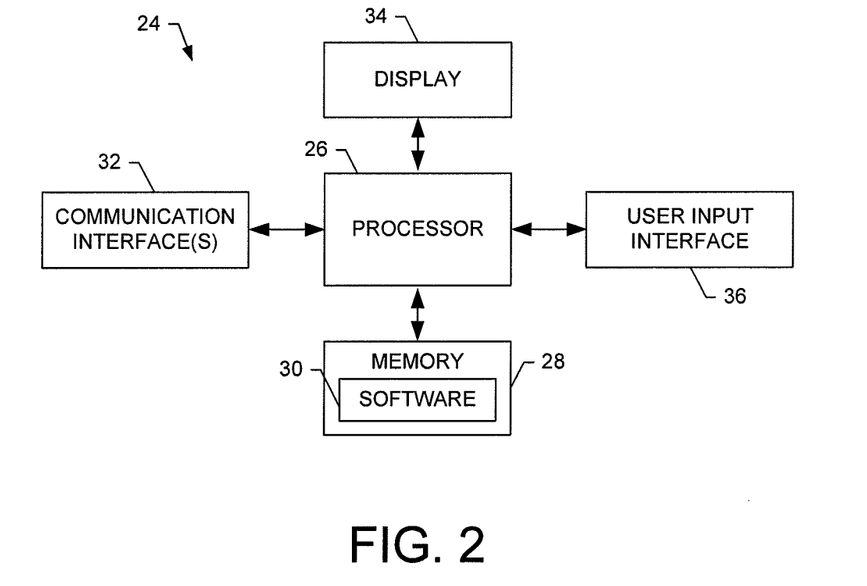
FIG. 2 is a schematic block diagram of an apparatus that may be configured to operate as a computing apparatus and/or server apparatus, in accordance with exemplary embodiments of the present invention.

Reference is now made to FIG. 2, which illustrates an apparatus 24 that may be configured to operate as a component of the system of FIG. 1, such as the computing apparatus 10, server apparatus 12 or digital pen 18 in accordance with exemplary embodiments of the present invention. Although shown as separate entities in FIG. 1, in some exemplary embodiments, a single apparatus may support multiple ones of the system components, logically separated but co-located within the apparatus. For example, a single apparatus may support both a computing apparatus and server apparatus. Additionally or alternatively, for example, a single apparatus may support both a server apparatus and database 14. Further, for example, a single apparatus may support both a computing apparatus and digital pen 18.

As shown in FIG. 2, the apparatus 24 includes various means for performing one or more functions in accordance with exemplary embodiments of the present invention, including those more particularly shown and described herein. It should be understood, however, that the apparatus may include alternative means for performing one or more like functions, without departing from the spirit and scope of the present invention. More particularly, for example, the apparatus may include a processor 26 connected to a memory 28. The memory may include volatile and/or non-volatile memory, and typically stores content, data or the like. In this regard, the memory may store one or more software applications 30, instructions or the like for the processor to perform various functions associated with operation of the apparatus in accordance with embodiments of the present invention. The memory may also store content transmitted from, and/or received by, the apparatus. As described herein, the software application(s) may each comprise software operated by the respective apparatuses. It should be understood, however, that in lieu of being implemented by a combination of hardware and software, any one or more of the software applications described herein may alternatively be implemented by hardware alone or in combination with firmware, without departing from the spirit and scope of the present invention.

In addition to the memory 28, the processor 26 may also be connected to at least one interface or other means for displaying, transmitting and/or receiving data, content or the like, such as in accordance with USB, RF, BT, IrDA, WLAN, LAN, MAN, WAN (e.g., Internet), PSTN techniques or the like. In this regard, the interface(s) may include at least one communication interface 32 or other means for transmitting and/or receiving data, content or the like. In addition to the communication interface(s), the interface(s) can also include at least one user interface that can include one or more earphones and/or speakers, a display 34, and/or a user input interface 36. The user input interface, in turn, can comprise any of a number of devices allowing the apparatus to receive data from a user, such as a microphone, a keypad, a touch-sensitive surface (integral or separate from the display), a joystick, a barcode reader, a radio frequency identification (RFID) reader or other input device. And further, in various exemplary embodiments, the digital pen 18 may be considered an example of a device allowing the apparatus to receive data from a user.

Figure 3:
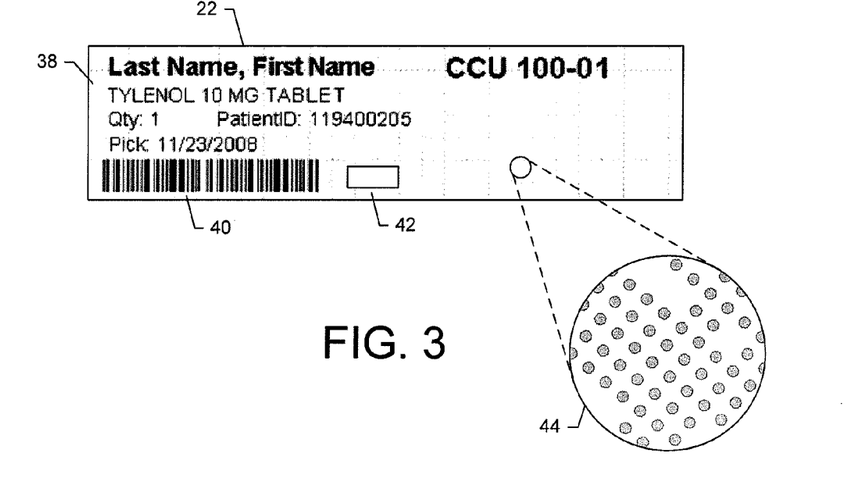
FIGS. 3-6 illustrate example labels according to exemplary embodiments of the present invention.
Figure 4:
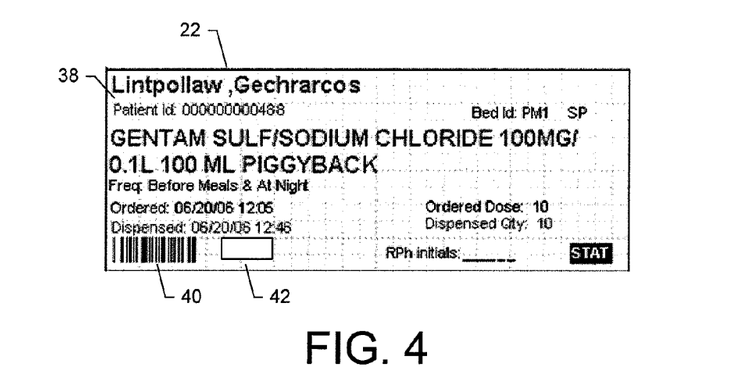
Figure 5:
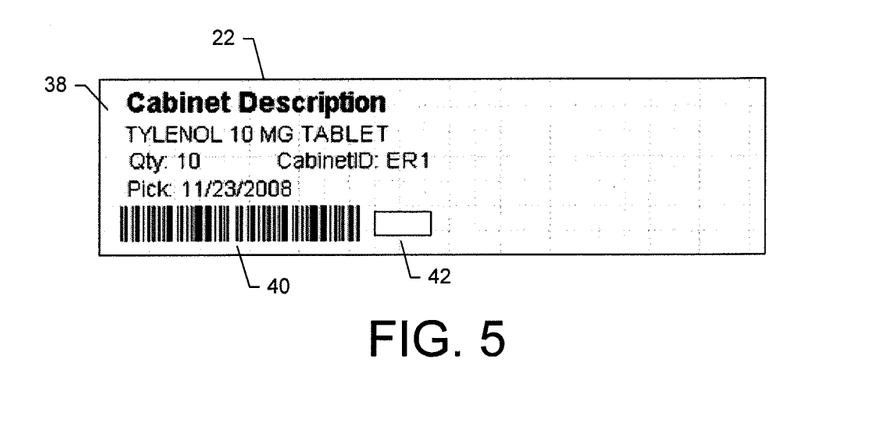
Figure 6:
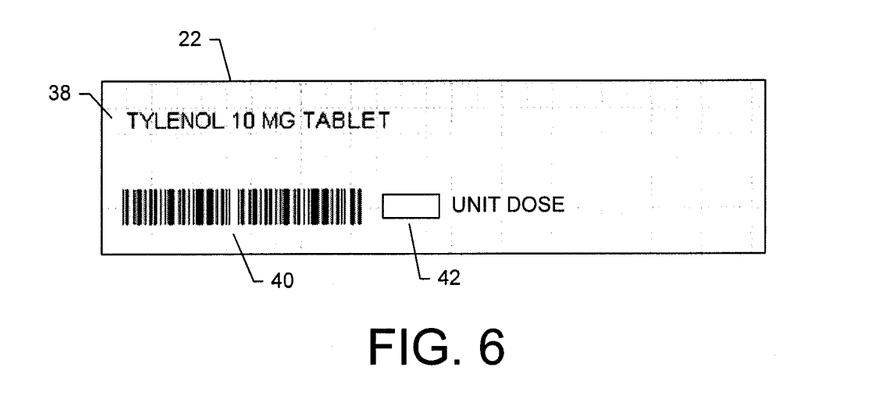

Returning now to FIG. 1, as explained above, the printer 16 may be configured to the print computing apparatus-generated labels 22 for the medication storage device and/or medication receptacles. Each label may include any of a number of different pieces of information related to a patient, medication, storage device or medication receptacle or the like. More particularly, for example, the label may include the name, dosage and/or quantity or amount of a medication in the particular medication storage device/receptacle. Additionally or alternatively, for example, the label may include a date/time the medication was picked from inventory, ordered and/or dispensed. Labels for patient orders may additionally or alternatively include the patient's name, identifier and/or location (e.g., within a medical facility), instructions for administration of the medication or the like. Other labels particular to medication storage devices may additionally or alternatively include a name or identifier of the respective medication storage device. Further, for example, the labels (whether for a patient or medication storage device) may include a barcode and/or RFID tag that encodes one or more of the pieces of information printed on the respective labels. Examples of various labels suitable for exemplary embodiments of the present invention are shown in FIGS. 3-6, which illustrate labels including various pieces of information 38, a barcode 40 and/or RFID tag 42. FIGS. 3 and 4 are examples of patient labels for medication receptacles destined for a particular patient; and FIGS. 5 and 6 are examples of labels for a medication storage device (e.g., cabinet, bin).

Even further, in various exemplary embodiments, the labels 22 may include a preprinted pattern 44 of machine-readable dots or other markings (a portion being shown in an exploded inset of the example label of FIG. 3) that enable the digital pen 18 to capture and digitize handwriting information input onto the labels. For example, the digital pen may include a digital camera configured to sense the preprinted pattern, from which the digital pen or computing apparatus 10 may determine the position of the digital pen. The digital camera may include one or more infrared light-emitting diodes (LED's) configured to illuminate the label, and include a light-sensitive (e.g., CCD, CMOS, etc.) sensor configured to record a two-dimensional image. In this regard, the preprinted pattern may be configured to absorb infrared light emitted by the infrared LED's in a mariner that illuminates the pattern to the light-sensitive sensor, which may be configured to record an image based upon the illuminated pattern.

Exemplary embodiments of the present invention extend use of the a label 22 beyond the mere presentation of various pieces of information related to the medication within the medication storage device or medication receptacle to which the label is affixed or otherwise associated. For example, the RFID tag 42 on the label permits locating or tracking the location of the medication storage device or medication receptacle. Also, for example, a preprinted pattern 44 of machine-readable dots or other markings permits capturing, digitizing and recording (storing) handwriting information input onto the labels. This handwriting information may include the handwritten signature, initials or other markings of a pharmacist, nurse or other user, whose handwriting information input onto the labels reflects verification of the contents of the medication storage device or medication receptacle. Additionally or alternatively, the handwriting information may include handwritten corrections or other changes to one or more pieces of information printed on a label.

In various example embodiments the system may include multiple digital pens 18, and the pens may be registered respective users. Registering the pens to respective users enables the system to authenticate handwriting information to a particular user according to the pen used to input the handwriting information onto the label 22, such as by comparing the registration of the pen to a set of permissions. Further, registering the pens to respective users may also facilitate locating or tracking the location of the medication storage device or medication receptacle to which the label is affixed or otherwise associated.

Figure 7:
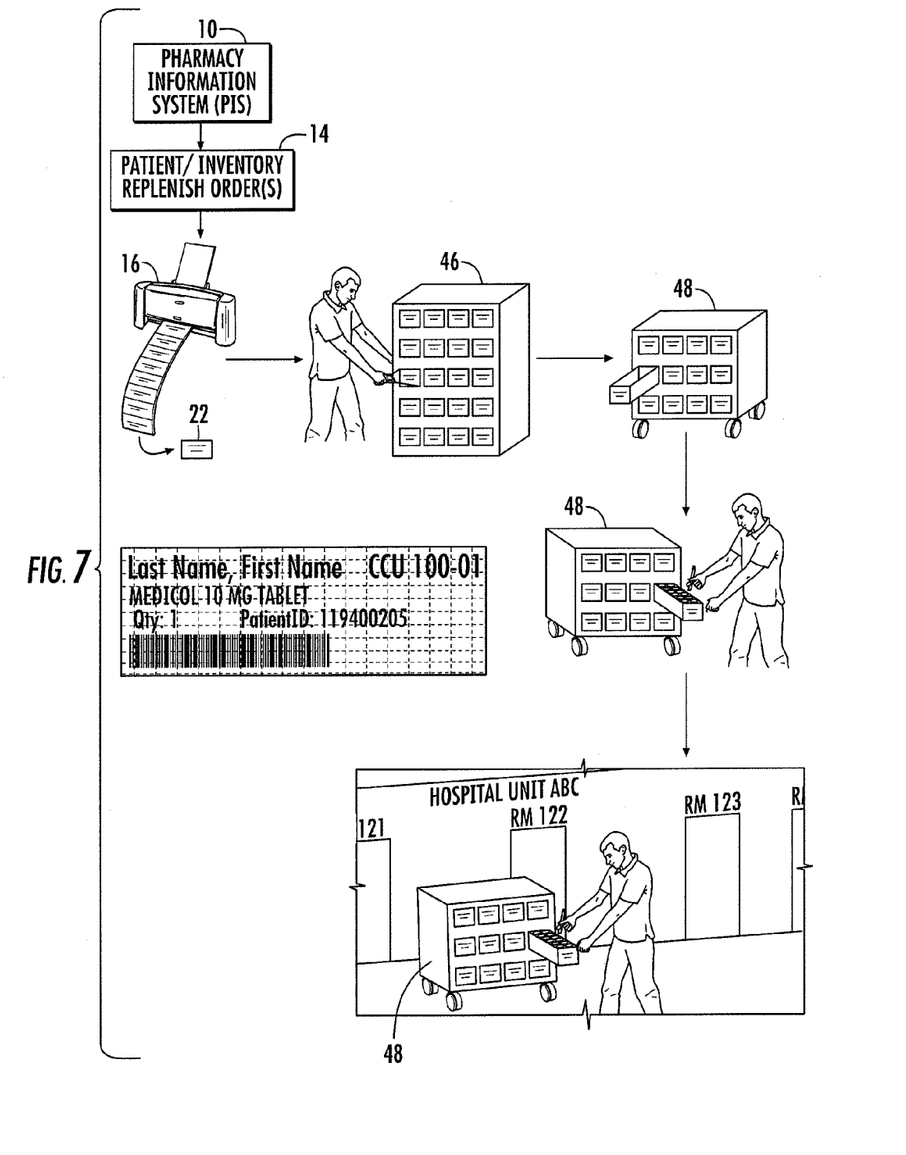
FIG. 7 illustrates a control flow diagram of a method of processing medication fill orders according to exemplary embodiments of the present invention, in accordance with exemplary embodiments of the present invention.

Reference is now made to FIG. 7, which illustrates a control flow diagram of a method of processing medication fill orders according to exemplary embodiments of the present invention. The method may include a pharmacy receiving one or more medication requests or prescriptions, which may be checked by a pharmacist and then entered into the pharmacy information system (PIS) (e.g., computing apparatus 10) as fill orders. The orders may specify one or more medications. The orders may include patient orders such as orders for a cart fill, first dose, "Stat" dose, "Now" dose or the like. Additionally or alternatively, in facilities that are partly or fully decentralized, the orders may include inventory replenish or restock orders for unit-based cabinets (UBC) including batch or immediate/critical low cabinets, satellite pharmacies, on demand or the like.

Regardless of the particular fill orders entered into the PIS 50 and stored in the database 14, the fill orders may then be recalled and processed. For example, a pharmacy technician may log into a computing apparatus 10 (the same or different from the PIS), and select an order for processing. The computing apparatus may receive the user's selection, and direct the printer 16 to print one or more labels 22 for the order. The technician may then affix the label(s) to appropriate medication receptacles into which the technician may place the medication(s) specified by the selected fill orders.

Medications from which the orders are filled may be stored in or on drawers, shelves, bins or the like (generally "compartments") of a stock medication storage device 46. Thus, the technician processing a fill order for one or more medications may locate the compartment(s) of the stock medication storage device that house the respective medication(s). The technician may then proceed to pick the medication(s) called for by the fill order and place those medication(s) in the appropriately-labeled medication receptacle(s). As the technician picks the medication(s), the technician may scan the barcode(s) 40 on the label(s) affixed to the medication receptacle(s), and may scan barcode(s) on label(s) affixed to the appropriate compartment(s) of the stock medication storage device. The scanning of the barcodes may be recorded by the PIS, and may be utilized for a number of different purposes such as to verify the that the appropriate medication has been picked to fill an order, to track inventory of the stock medication storage device, or the like. In this regard, the PIS may store and maintain an order log for each fill order, and information related to the scanning of the barcodes may be recorded in the order log for the particular fill order, where each entry in the order log may relate to a particular event or activity with respect to the order and may be date/time stamped.

Also, in various instances as the technician processes the fill order, the technician may correct or change one or more pieces of information printed on a label 22. For example, in various instances the quantity ordered may not equal the quantity being filled, such as in instances in which the stock medication storage device 46 does not include a sufficient quantity of the medication. In these instances, the technician may utilize a digital pen 18 to handwrite a correction to the quantity directly on the label 22 for the respective medication. When the label includes a preprinted pattern 44 of machine-readable dots or other markings, the handwritten correction may be additionally captured, digitized and recorded, such as in the order log for the particular fill order. Additionally, if the digital pen is registered to the technician, the technician may be authenticated as having authority to record a correction or change to the fill order, and/or the name or another identifier of the technician making the correction may be recorded in the order log as being associated with the correction. The technician and any others may be authenticated in a number of different manners, such as by comparing the registration of the pen of the technician/other users to a set of permissions associated with or otherwise bound to the order log.

The correction handwritten on the label 22 may be recorded in any of a number of different manners. For example, the correction may be recorded by overlaying an image of the handwritten correction on an image of the label. Additionally or alternatively, handwriting information captured proximate or overlaying a known location of the quantity information on a label may be interpreted as a correction to the quantity information. In these instances, the handwriting information may be converted to text such as by optical character recognition, and recorded in the order log as a correction to the quantity.

As the technician completes fill orders, the technician may load the receptacles for the completed fill orders onto a cart 48 or other mobile medication storage device for transport to one or more patients or, for inventory replenish or restock orders, one or more unit-based cabinets, satellite pharmacies or the like.

Before the cart 48 is transported from the pharmacy, however, a pharmacist may verify that the completed fill orders are correct, such as by comparison of the labels 22 to the medications within the respective medication receptacles. The pharmacist may then indicate orders that have been verified as correct, such as by signing, initialing or otherwise marking the label utilizing a digital pen 18. In such instances, the pharmacist's signature, initials or other marking may be captured, digitized and recorded, such as in the order logs for the respective fill orders. Similar to the technician, if the digital pen is registered to the pharmacist, the pharmacist may be authenticated as having authority verify a fill order, and/or the name or another identifier of the pharmacist verifying the fill orders may be recorded in the order logs as being associated with the verification. Also as with the technician, the pharmacist's signature, initials or other marking may be recorded in any of a number of different manners, such as in the form of an image that may, but need not, overlay an image of the label.

After the pharmacist has verified the completed fill orders, the cart 48 including the receptacles for the completed fill orders may be transported to one or more patients or, for inventory replenish or restock orders, one or more unit-based cabinets, satellite pharmacies or the like. As the cart is transported, in instances in which the labels 22 are equipped with RFID tags 42, the receptacles to which the labels are affixed may be located or tracked based on the respective RFID tags. And if so desired, at one or more instances, the current location of one or more of the receptacles may be recorded in the appropriate order log(s).

The receptacles may be located or tracked in any of a number of different manners. For example, a hospital, nursing home, or other similar institution within which the cart is transported may include a radio frequency (RF) network operable within the institution. The network, in turn, may include plurality of access points, RFID interrogators or the like, which may be located at known locations within the institution. In such instances, a receptacle may be located or tracked based on communication of its RFID tag with the network, and more particularly with one or more of the access points, interrogators or the like of the network. Locating or tracking a receptacle may be accomplished, for example, based on a comparison of signal strength(s) of the tag with one or more access points/interrogators and identifying the location of the access point/interrogator having the greatest signal strength. As another example, locating or tracking a receptacle may be accomplished in accordance with triangulation techniques based on timing signals from the RFID tags received by multiple ones of the access points/interrogators.

The destination for the completed fill orders on the cart 48 may differ depending on whether the orders are for patients or are for restocking unit-based cabinets, satellite pharmacies or the like. As shown in FIG. 7, a patient order may be transported to patients such as by a nurse who dispenses the medications to the patients. Alternatively, an inventory replenish or restock order may be transported to a particular cabinet, or to a medication storage device at a satellite pharmacy by a nurse or other medical or pharmacy personnel. The cart may be transported directly to its destination, or in various embodiments, may pass through a number of different intermediate points between the pharmacy and its destination, at which points the cart may be received by medical personnel who transport the cart to the next point or pass the cart to other medical personnel who transport the cart to the next point. For example, a cart destined for patients may pass to a nurse at a nurse's station on a floor of a hospital, at which point a nurse stationed on the floor may take the cart and transport it to patients on the floor.

As a receptacle is received at an intermediate point and/or the medication in the receptacle is dispensed, the nurse or other personnel at the intermediate point or destination may acknowledge receiving the receptacle or dispensing the medication, such as by using a digital pen 18 registered to the nurse or other personnel in a manner similar to the pharmacist verifying the completed fill orders (including, e.g., authenticating the nurse or other personnel as having the appropriate authority). Additionally, in various instances, the nurse or other personnel may further correct or change one or more pieces of information printed on the respective label 22, such as in a manner similar to the technician processing the fill order. In these instances, the acknowledgement, correction or change may be recorded in the order log for the respective fill order.

As explained above, a fill order may have an order log that includes a number of recorded, date/time stamped events or activities related to the fill order. Initially, for example, the order log may include details of the fill order including any of a number of different pieces of information that may be printed on a label 22 for the order. The order log may additionally include an image or other digital representation of the label. Also, for example, the order log may include information encoded into the barcode of a compartment of the stock medication storage device 46 from which medication(s) picked for the order were stored, and may include a date/time stamp reflecting the time when the technician scanned the respective barcode. The order log for a fill order may also include handwriting information reflecting handwriting on the label. Further, for example, the order log may include the current location of the respective receptacle at one or more instances.

The handwriting information recorded in an order log may include, corrections/changes handwritten by the technician processing the order, and the name/identifier of the respective technician. Additionally or alternatively, the handwriting information may include the signature, initials or other marking of a pharmacist verifying the fill order. Further, the handwriting information may include acknowledgment of removal of the respective receptacle from its cart, and any further corrections/changes handwritten by the nurse or other personnel dispensing the medication(s), and the name/identifier of the respective nurse/personnel.

In addition to permitting digital capture of handwriting information from various users, registering digital pens 18 to the respective users may permit authenticating handwriting information to a particular user according to the pen used to input the handwriting information onto the label 22. Registering the pens to respective users may also facilitate locating or tracking the location of the medication receptacle to which the label is affixed or otherwise associated. In this regard, different users may work or be otherwise associated with in different departments or areas of an institution. By reviewing the order log and identifying the user who entered the last handwriting input recorded for the order log, one may be able to identify the location of the receptacle as being the department/area of the respective user, or may otherwise narrow-down possible locations of the receptacle based on the department/area of the respective user.

As suggested above, the order log for a fill order may be utilized in a number of different manners to locate or track a receptacle. Additionally or alternatively, however, the order log may be used to implement a number of analytics related to the processing, verification, transport and/or dispensing of the fill order. These analytics, then, may be reviewed for a number of different purposes, such as productivity, quality control or the like.

As explained above, the digital pen 18 has the capability to capture and digitize handwritten information. In various instances, however, the digital pen may also include more advanced functionality from which exemplary embodiments of the present invention may benefit. Two examples of such functionality are the ability to interpret digital pen "tags" and "pidgets." A digital Pen tag is generally a handwritten character, icon or other marking that is interpretable by the system to perform a particular function, whereas a pidget is generally a dedicated micro-dot patterns that represent a global function such as a calculator.

According to further exemplary embodiments, advanced digital pen functionality may be implemented in any of a number of different manners. For example, a handwritten, circled letter "e" may be utilized by a user to designate an error on a label 22, and may be interpretable by a computing apparatus 10 to produce (on its display) a list of selectable error codes. The user may then operate the computing device to select an appropriate error code, which may then be recorded in the respective order log.

In another example, a digital pen pidget may be used to drive a computing apparatus 10 to define a number of objects or perform a number of functions. These functions may include, for example, searching or browsing fill orders or order logs, such as for received, completed or rejected fill orders. Thus, for example, when a nurse or other user is viewing a fill order for a patient and notices a mistake, the nurse may tap a search pidget and then the appropriate label 22 with the nurse's digital pen 18, which may be interpreted by a computing apparatus 10 to recall and produce (on its display) the order log details for that patient.

According to one aspect of the present invention, all or a portion of the components of exemplary embodiments of the present invention, such as the computing apparatus 10, server apparatus 12 and/or digital pen 18, generally operate under control of a computer program. The computer program for performing the methods of exemplary embodiments of the present invention may include one or more computer-readable program code portions, such as a series of computer instructions, embodied or otherwise stored in a computer-readable storage medium, such as the non-volatile storage medium.

It will be understood that methods, systems and computer programs according to exemplary embodiments of the present invention may be implemented by various means, such as hardware, firmware, and/or software including one or more computer program instructions. As will be appreciated, any such computer program instructions may be loaded onto a computer or other programmable apparatus to produce a machine, such that the instructions which execute on the computer or other programmable apparatus (e.g., hardware) create means for implementing the functions specified in the block(s) or step(s) of the flowcharts. These computer program instructions may also be stored in a computer-readable memory that may direct a computer or other programmable apparatus to function in a particular manner, such that the instructions stored in the computer-readable memory produce an article of manufacture including instruction means which implement functions specified herein. The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing functions specified herein.

Accordingly, blocks or steps of the flowcharts support combinations of means for performing the specified functions, combinations of steps for performing the specified functions and program instruction means for performing the specified functions. It will also be understood that one or more blocks or steps of the flowcharts, and combinations of blocks or steps in the flowcharts, may be implemented by special purpose hardware-based computer systems which perform the specified functions or steps, or combinations of special purpose hardware and computer instructions.

Many modifications and other embodiments of the invention will come to mind to one skilled in the art to which this invention pertains having the benefit of the teachings presented in the foregoing descriptions and the associated drawings. It should therefore be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus comprising a processor configured to at least perform or cause the apparatus to at least perform the following:
    storing an order log for a fill order specifying a medication, wherein the fill order being completed includes producing a receptacle including the medication, the receptacle including an affixed label having, printed thereon, one or more pieces of information related to the fill order, and a pattern of machine-readable dots or markings enabling capture and digitization of handwriting information input onto the label; and
    recording, in the order log, one or more events or activities related to the fill order, wherein recording one or more events or activities includes:
        receiving a digitized signature, initials or marking handwritten on the label and captured by a digital pen based on the pattern of machine-readable dots or markings printed on the label, wherein the digital pen is registered to a user, and wherein the signature, initials or marking reflect verification by the user that the medication in the receptacle is correct relative to the fill order;
        authenticating the user as having authority to verify the fill order based on the registration of the digital pen to the user; and
        recording the digitized signature, initials or marking in the order log when the user is authenticated.

2. The apparatus of claim 1, wherein the digital pen capturing the signature, initials or marking handwritten on the label comprises a first digital pen, wherein recording one or more events or activities further includes:
    receiving a digitized correction or change to information on the label, the correction or change having been handwritten on the label and captured by a second digital pen based on the pattern of machine-readable dots or markings printed on the label, wherein the second digital pen is registered to a second user, and wherein the correction or change reflects a correction or change to one or more of the pieces of information printed on the label;
    authenticating the second user as having authority to correct or change the fill order based on the registration of the second digital pen to the second user; and
    recording the correction or change in the order log when the second user is authenticated.

3. The apparatus of claim 1, wherein the digital pen capturing the signature, initials or marking handwritten on the label comprises a first digital pen, wherein recording one or more events or activities further includes:
    receiving a digitized first acknowledgement handwritten on the label and captured by a second digital pen based on the pattern of machine-readable dots or markings printed on the label, wherein the second digital pen is registered to a second user, and wherein the first acknowledgement reflects receipt of the receptacle by the second user;
    recording the first acknowledgement in the order log;
    receiving a digitized second acknowledgement handwritten on the label and captured by a third digital pen based on the pattern of machine-readable dots or markings printed on the label, wherein the third digital pen is registered to a third user, and wherein the second acknowledgement reflects dispensing of the medication in the receptacle by the third user; and
    recording the second acknowledgement in the order log.

4. The apparatus of claim 3, wherein the first, second and third users are associated with respective first, second and third areas of an institution, wherein the processor is further configured to perform, cause the apparatus to perform or facilitate performance of the following:
    locating the receptacle after recording one of the digitized signature, initials or marking, recording the first acknowledgement or recording the second acknowledgement,
    wherein the receptacle is located relative to the first, second or third area based on the signature, initials or marking, first acknowledgment or second acknowledgement of the first, second or third user having been recorded before locating the receptacle.

5. The apparatus of claim 1, wherein the label affixed to the receptacle further includes a radio frequency identification (RFID) tag configured to encode one or more of the pieces of information printed on the label, and wherein recording one or more events or activities further includes:

locating the receptacle within an institution at one or more instances based on communication of the RFID tag with a radio frequency (RF) network operable within the institution; and recording the location of the receptacle at the one or more instances in the order log.

6. A method comprising:

storing, in a computer-readable storage medium, an order log for a fill order specifying a medication, wherein the fill order being completed includes producing a receptacle including the medication, the receptacle including an affixed label having, printed thereon, one or more pieces of information related to the fill order, and a pattern of machine-readable dots or markings enabling capture and digitization of handwriting information input onto the label; and recording, in the order log, one or more events or activities related to the fill order, wherein recording one or more events or activities includes:

receiving a digitized signature, initials or marking handwritten on the label and captured by a digital pen based on the pattern of machine-readable dots or markings printed on the label, wherein the digital pen is registered to a user, and wherein the signature, initials or marking reflect verification by the user that the medication in the receptacle is correct relative to the fill order;

authenticating the user as having authority to verify the fill order based on the registration of the digital pen to the user; and recording the digitized signature, initials or marking in the order log when the user is authenticated.

7. The method of claim 6, wherein the digital pen capturing the signature, initials or marking handwritten on the label comprises a first digital pen, wherein recording one or more events or activities further includes:

receiving a digitized correction or change to information on the label, the correction or change having been handwritten on the label and captured by a second digital pen based on the pattern of machine-readable dots or markings printed on the label, wherein the second digital pen is registered to a second user, and wherein the correction or change reflects a correction or change to one or more of the pieces of information printed on the label;

authenticating the second user as having authority to correct or change the fill order based on the registration of the second digital pen to the second user; and recording the correction or change in the order log when the second user is authenticated.

8. The method of claim 6, wherein the digital pen capturing the signature, initials or marking handwritten on the label comprises a first digital pen, wherein recording one or more events or activities further includes:

receiving a digitized first acknowledgement handwritten on the label and captured by a second digital pen based on the pattern of machine-readable dots or markings printed on the label, wherein the second digital pen is registered to a second user, and wherein the first acknowledgement reflects receipt of the receptacle by the second user;

recording the first acknowledgement in the order log;

receiving a digitized second acknowledgement handwritten on the label and captured by a third digital pen based on the pattern of machine-readable dots or markings printed on the label, wherein the third digital pen is registered to a third user, and wherein the second acknowledgement reflects dispensing of the medication in the receptacle by the third user; and recording the second acknowledgement in the order log.

9. The method of claim 8, wherein the first, second and third users are associated with respective first, second and third areas of an institution, and wherein the method further comprises:

locating the receptacle after recording one of the digitized signature, initials or marking, recording the first acknowledgement or recording the second acknowledgement, wherein the receptacle is located relative to the first, second or third area based on the signature, initials or marking, first acknowledgment or second acknowledgement of the first, second or third user having been recorded before locating the receptacle.

10. The method of claim 6, wherein the label affixed to the receptacle further includes a radio frequency identification (RFID) tag configured to encode one or more of the pieces of information printed on the label, and wherein recording one or more events or activities further includes:

locating the receptacle within an institution at one or more instances based on communication of the RFID tag with a radio frequency (RF) network operable within the institution; and recording the location of the receptacle at the one or more instances in the order log.

11. A computer-readable storage medium having computer-readable program code portions stored therein that in response to execution by a processor, cause an apparatus to at least perform the following:

storing, in a computer-readable storage medium, an order log for a fill order specifying a medication, wherein the fill order being completed includes producing a receptacle including the medication, the receptacle including an affixed label having, printed thereon, one or more pieces of information related to the fill order, and a pattern of machine-readable dots or markings enabling capture and digitization of handwriting information input onto the label; and recording, in the order log, one or more events or activities related to the fill order, wherein recording one or more events or activities includes:

receiving a digitized signature, initials or marking handwritten on the label and captured by a digital pen based on the pattern of machine-readable dots or markings printed on the label, wherein the digital pen is registered to a user, and wherein the signature, initials or marking reflect verification by the user that the medication in the receptacle is correct relative to the fill order;

authenticating the user as having authority to verify the fill order based on the registration of the digital pen to the user; and recording the digitized signature, initials or marking in the order log when the user is authenticated.

12. The computer-readable storage medium of claim 11, wherein the digital pen capturing the signature, initials or marking handwritten on the label comprises a first digital pen, wherein recording one or more events or activities further includes:

receiving a digitized correction or change to information on the label, the correction or change having been handwritten on the label and captured by a second digital pen based on the pattern of machine-readable dots or markings printed on the label, wherein the second digital pen is registered to a second user, and wherein the correction or change reflects a correction or change to one or more of the pieces of information printed on the label;

authenticating the second user as having authority to correct or change the fill order based on the registration of the second digital pen to the second user; and recording the correction or change in the order log when the second user is authenticated.

13. The computer-readable storage medium of claim 11, wherein the digital pen capturing the signature, initials or marking handwritten on the label comprises a first digital pen, wherein recording one or more events or activities further includes:

receiving a digitized first acknowledgement handwritten on the label and captured by a second digital pen based on the pattern of machine-readable dots or markings printed on the label, wherein the second digital pen is registered to a second user, and wherein the first acknowledgement reflects receipt of the receptacle by the second user;

recording the first acknowledgement in the order log;

receiving a digitized second acknowledgement handwritten on the label and captured by a third digital pen based on the pattern of machine-readable dots or markings printed on the label, wherein the third digital pen is registered to a third user, and wherein the second acknowledgement reflects dispensing of the medication in the receptacle by the third user; and recording the second acknowledgement in the order log.

14. The computer-readable storage medium of claim 13, wherein the first, second and third users are associated with respective first, second and third areas of an institution, wherein the computer-readable storage medium has computer-readable program code portions stored therein that in response to execution by the processor, cause the apparatus to further perform the following:

locating the receptacle after recording one of the digitized signature, initials or marking, recording the first acknowledgement or recording the second acknowledgement, wherein the receptacle is located relative to the first, second or third area based on the signature, initials or marking, first acknowledgment or second acknowledgement of the first, second or third user having been recorded before locating the receptacle.

15. The computer-readable storage medium of claim 11, wherein the label affixed to the receptacle further includes a radio frequency identification (RFID) tag configured to encode one or more of the pieces of information printed on the label, and wherein recording one or more events or activities further includes:

locating the receptacle within an institution at one or more instances based on communication of the RFID tag with a radio frequency (RF) network operable within the institution; and recording the location of the receptacle at the one or more instances in the order log.

16. A system comprising:

a first digital pen registered to a first user and configured to capture and digitize a handwritten signature, initials or marking from a label based on a pattern of machine-readable dots or markings printed on the label, wherein the label is affixed to a receptacle including a medication, the receptacle having been produced to complete a fill order specifying the medication, the label also having one or more pieces of information related to the fill order printed thereon;

a second digital pen registered to a second user and configured to capture and digitize a handwritten correction or change to information on the label based on the pattern of machine-readable dots or markings printed on the label; and a computing apparatus configured to store an order log for the fill order, wherein the computing apparatus is also configured to record, in the order log, one or more events or activities related to the fill order, wherein being configured to record one or more events or activities includes being configured to:

receive the digitized signature, initials or marking reflecting verification by the first user that the medication in the receptacle is correct relative to the fill order;

authenticate the first user as having authority to verify the fill order based on the registration of the digital pen to the first user;

record the digitized signature, initials or marking in the order log when the first user is authenticated;

receive the digitized correction or change to information on the label, the correction or change reflecting a correction or change to one or more of the pieces of information printed on the label;

authenticate the second user as having authority to correct or change the fill order based on the registration of the second digital pen to the second user; and record the correction or change in the order log when the second user is authenticated.

17. The system of claim 16, wherein the the second digital pen is configured to capture and digitize a first acknowledgement based on the pattern of machine-readable dots or markings printed on the label; and wherein the system further comprises:

a third digital pen registered to a third user and configured to capture and digitize a second acknowledgement based on the pattern of machine-readable dots or markings printed on the label;

wherein the computing apparatus being configured to record one or more events or activities further includes being configured to:

receive the digitized first acknowledgement reflecting receipt of the receptacle by the second user;

record the first acknowledgement in the order log;

receive the digitized second acknowledgement reflecting dispensing of the medication in the receptacle by the third user; and recording the second acknowledgement in the order log.

18. The system of claim 17, wherein the first, second and third users are associated with respective first, second and third areas of an institution, wherein the computing apparatus is further configured to locate or facilitate locating the receptacle after recording one of the digitized signature, initials or marking, recording the first acknowledgement or recording the second acknowledgement, and wherein the receptacle is locatable relative to the first, second or third area based on the signature, initials or marking, first acknowledgment or second acknowledgement of the first, second or third user having been recorded before locating the receptacle.

19. The system of claim 16, wherein the label affixed to the receptacle further includes a radio frequency identification (RFID) tag configured to encode one or more of the pieces of information printed on the label, and wherein the computing apparatus being configured to record one or more events or activities further includes being configured to:

locate the receptacle within an institution at one or more instances based on communication of the RFID tag with a radio frequency (RF) network operable within the institution; and
record the location of the receptacle at the one or more instances in the order log.

* * * * *